(12) United States Patent
Borody

(10) Patent No.: US 6,426,338 B1
(45) Date of Patent: Jul. 30, 2002

(54) THERAPY FOR CONSTIPATION

(76) Inventor: Thomas Julius Borody, 144 Great North Road, Five Dock NSW 2046 (AU)

( * ) Notice: Subject to any disclaimer, the term of this patent is extended or adjusted under 35 U.S.C. 154(b) by 0 days.

(21) Appl. No.: 09/403,780
(22) PCT Filed: May 7, 1998
(86) PCT No.: PCT/AU98/00332
§ 371 (c)(1),
(2), (4) Date: Dec. 17, 1999
(87) PCT Pub. No.: WO98/50043
PCT Pub. Date: Nov. 12, 1998

(30) Foreign Application Priority Data

May 7, 1997 (AU) ................................................ P06653

(51) Int. Cl.$^7$ ......................... A61K 31/60; A61K 31/16; A61K 31/635; A01N 37/36
(52) U.S. Cl. ........................................ 514/159; 166/629
(58) Field of Search ................................ 514/159, 166, 514/629, 33

(56) References Cited

U.S. PATENT DOCUMENTS 5,519,014 A * 5/1996 Borody ........................ 514/159

OTHER PUBLICATIONS

Verne, G. N., et al., Gastroenterology 108, A705 (1995).
CAPLUS Abstract 1996 : 305722 of Calguneri, M., et al., Mediterranean Congr. Rheumatol., 7$^{th}$ (1995), Ed. Boki, K. A., Monduzzi Editore (Bologna, Italy), pp 181–184.
Crotty, B., et al., Gut, 33, 59–64 (1992).
Verne, G. N., et al., Digestive Diseases and Sciences, vol. 43 No. 9, pp 1959–1963 (9/97).
Sandyk, R., et al., J. of the Royal Soc. of Medicine, vol. 77 (12), p 1066 (12/84).
Crotty, B., et al., Gut, 33, 1353–1357 (1992).
Mourelle, M., et al., Biochemical Pharmacology, vol. 36, No. 18, 3021–3025 (1978).

* cited by examiner

*Primary Examiner*—Frederick Krass
*Assistant Examiner*—Donna Jagoe

(57) ABSTRACT

Compositions comprising colchicine and at least one aminosalicylic acid derivative, preferably olsalazine is used for treatment of prophylaxis of constipation.

5 Claims, No Drawings

THERAPY FOR CONSTIPATION

This application is a 371 of PCT/AU98/00332 filed May 7, 1998.

1. Technical Field

This invention relates to methods and compositions for the treatment of bowel disorders characterised by constipation. Such disorders include segments of Irritable Bowel Syndrome (IBS) characterised by constipation, chronic pseudo-obstruction, chronic abdominal bloating syndrome and functional constipation. Symptoms include abdominal pain, constipation, bloating, acid reflux, flatulence, nausea and vomiting, chronic lethargy and sleep disorders.

2. Background Art

Constipation is a very common condition in the west, affecting about 20% of the population. Yet, to date no effective therapy is available. Chronic constipation is a condition largely confined to women and is of unknown etiology. Diet, psychology, motility disturbances and enteric nervous dysplasia have been identified as possible causes or factors. However, for the majority of patients the cause of constipation remains obscure. The pathogenesis of irritable bowel syndrome has also hitherto been unknown. Conventional treatments have been unsatisfactory as instanced by the very large number of therapies available and recommended from time to time. These have included psychotherapy, dietary regimens, and laxatives. To date, there is no evidence that any such therapies influence the underlying mechanism of the disorder and certainly cure is not possible.

In general, therefore, the treatment of constipation and bloating as well as pseudo-obstruction and functional constipation depends still on chronic usage of laxatives. There has indeed been little attempt to treat any underlying pathophysiologic condition, since the underlying condition is not yet understood. However, as described by Borody T J et al (Oral vancomycin can reverse idiopathic constipation, *Gastroenterology* (1989) 96 52A) there is some evidence that in constipated patients abnormal bowel flora may be invaded by yet uncharacterised pathogenic bacteria which manufacture false neurotransmitters which bind to the nerves and muscle fibres of the enteric nervous system and affect intestinal motility. Constipation and pseudo-obstruction may ensue from such an infection. From clinical observations and response to antibiotics it is apparent that more often than not constipation is caused by an infection of the normal enteric flora by bacteria which manufacture endorphin-like substances.

However, use of antibiotics on a long-term basis has been of little help in solving the problem of constipation because of potential side-effects. For example, vancomycin is neurotoxic. Furthermore, costs of such antibiotics to the patient would be prohibitive.

More recently, colchicine, a drug used for several decades in the treatment of gout and one known to cause diarrhoea, has been trialed in severe constipation (Verne G N et al: Colchicine is an effective treatment for patients with severe idiopathic constipation, *Gastroenterology* (1995) 108 A705). However, colchicine given alone in the doses described in the paper is dangerous long-term since it can cause muscle and nerve damage (myopathy and neuropathy) and is therefore of no practical use in chronic constipation. In a lower dose it is insufficient in most patients to stimulate defecation. Hence, on its own colchicine is clinically of interest but of no practical use for this group of conditions.

Australian patent no. 652191 discloses the usefulness of salicylic acid derivatives in the treatment of bowel disorders including constipation. However, only larger doses of 1.0 to 1.5 g amino-salicylic acid derivatives effectively relieved the symptoms of constipation and the percentage of patients whose constipation is actually ameliorated by administration of amino-salicylic acid derivatives alone is relatively low.

Accordingly, there remains a need for an effective therapy for constipation. It is an object of the present invention to provide a composition and method for the treatment of constipation.

DISCLOSURE OF THE INVENTION

The present invention arose from observations by the inventor that treatment of patients with colchicine for constipation, although effective, requires high doses as does treatment with amino-salicylic acid derivatives. It was only upon combining both these agents at lower doses that it was observed that such a combination produces the best results to date for the patient. The clinical effect on the symptoms of bowel disorders characterised by constipation, by combined administration of low doses of an amino-salicylic acid derivative and colchicine, is surprisingly greater than would be expected from a summation of the known effects of administering the same doses of either the amino-salicylic acid derivative or colchicine alone.

Thus, in a first embodiment, the invention provides a pharmaceutical composition for the treatment or prophylaxis of constipation, the composition including or consisting of colchicine and at least one amino-salicylic acid derivative.

In a second embodiment, the invention provides a method for the treatment or prophylaxis of constipation in a mammal in need of said treatment or prophylaxis, including administering to said mammal an effective amount of colchicine and an effective amount of at least one amino-salicylic acid derivative.

The invention further provides a process of manufacturing a medicament for the treatment or prophylaxis of constipation, the composition including or consisting of colchicine and at least one amino-salicylic acid derivative; use of a composition including or consisting of colchicine and at least one amino-salicylic acid derivative for the treatment or prophylaxis of constipation; and use of colchicine with at least one amino-salicylic acid derivative for the manufacture of a medicament for the treatment or prophylaxis of constipation.

As used herein, the expression "amino-salicylic acid derivative" means 4-amino salicylic acid, 5-amino salicylic acid, or a pharmaceutically acceptable salt or prodrug thereof.

In the compositions, methods, processes and uses in accordance with the invention, the amino-salicylic acid derivative is typically selected from the group consisting of mesalazine (5-amino salicylic acid), olsalazine, sulfasalazine, ipsalazide, balsalazide, benzalazine, para-amino salicylic acid (4-amino salicylic acid) and pharmaceutically acceptable salts thereof.

Preferably, the amino-salicylic acid derivative is one of a group consisting of sulfasalazine, olsalazine and the amino salicylic acids including 5-amino salicylic acid and 4-amino salicylic acid or a pharmaceutically acceptable salt thereof. Still more preferably, the amino-salicylic acid derivative is selected from mesalazine, olsalazine and pharmaceutically acceptable salts thereof. Advantageously, the amino-salicylic acid derivative may be selected by reference to the particular disorder involved. For example, pain-predominant constipation may benefit more from administration of a preparation including mesalazine as opposed to olsalazine.

Compositions which include colchicine and more than one amino-salicylic acid derivative are also within the scope of the present invention. Similarly, a method of the second embodiment of the invention may include administering more than one amino-salicylic acid derivative.

Compositions of the invention may be prepared by means known in the art for the preparation of pharmaceutical compositions including blending, grinding, homogenising, suspending, dissolving, emulsifying, dispersing and, where appropriate, mixing of the colchicine and amino-salicylic acid derivative(s), optionally together with one or more selected excipients, diluents, carriers and adjuvants.

The pharmaceutical composition of the invention may be in the form of a tablet, lozenge, pill, troche, capsule, soft-gel capsule, sachet or other combining vehicle, elixir, powder, including lyophilised powder, solution, granule, suspension, emulsion, syrup or tincture. Slow-release, or delayed-release, forms may also be prepared, for example in the form of coated particles, multi-layer tablets or microgranules. The composition may also be presented in a compliance-enhancing blister pack.

Solid forms for oral administration may contain pharmaceutically acceptable binders, sweeteners, disintegrating agents, diluents, flavourings, coating agents, preservatives, lubricants and/or time delay agents. Suitable binders include gum acacia, gelatin, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, xanthan gum, betonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitble coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further include dispersing agents and/or suspending agents. Suitable suspending agents include sodium carboxymethylcellulose, methylcellulose, hydroxypropylmethyl-cellulose, polyvinyl-pyrrolidone, sodium alginate or cetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

Emulsions for oral administration may further include one or more emulsifying agents. Suitable emulsifying agents include dispersing agents as exemplified above or natural gums such as gum acacia or gum tragacanth.

A composition of the first embodiment typically contains from 0.1 mg to 3 mg of colchicine, more typically from 0.5 mg to 2.0 mg, even more typically from 0.5 mg to 1.5 mg; and from 100 mg to 1000 mg, more typically from 200 mg to 500mg, even more typically from 250 mg to 400 mg of the amino-salicylic acid derivative.

For administration as a tablet or capsule, the colchicine and amino-salicylic acid derivative may be combined in powdered or granulated form, for example by compression into a tablet or as a filling for a capsule. Alternatively, the composition of the first embodiment may be provided in the form of a tablet/capsule containing one or both of the colchicine and amino-salicylic acid derivative in a microencapsulated form. As another possibility, the composition of the first embodiment may be provided in the form of a tablet/capsule containing the colchicine or the amino-salicylic acid derivative in a powdered form, and the other in a microencapsulated form. As a further possibility, the composition of the first embodiment may be provided in the form of a tablet/capsule containing the colchicine and the amino-salicylic acid derivative each in a microencapsulated form. In even further possibilities, the composition of the first embodiment may be provided in the form of a tablet containing the colchicine or the amino-salicylic acid derivative within a capsule containing the other, a capsule containing one of the colchicine or amino-salicylic acid derivative in a tablet of the other, or a capsule containing the colchicine or the amino-salicylic acid derivative within an outer capsule containing the other.

Preferably, the amino-salicylic acid derivative is presented in a form which facilitates its release in the distal small bowel. For example, in a composition of the invention, the amino-salicylic acid derivative may be provided with an enteric coating or provided in an enteric coated release capsule, or enteric coated colchicine microencapsulated particles can be carried within a capsule of distally-releasing amino-salicylic acid, for example olsalazine. When the colchicine is administered in a relatively high dosage, such as for example 1.5 mg per day or more, it is essential that the colchicine be enterically coated.

Suitable materials for enteric coating are known in the art and include various synthetic resins bearing carboxyl groups, phenyl salicylate, and shellac. Examples of such enteric coating materials are polymethacrylic acid and methacrylic acid copolymers such as methacrylic acid—acrylic acid ester copolymers; modified cellulose esters such as hydroxypropyl cellulose phthalate, hydroxypropyl methylcellulose phthalate, ethyl cellulose phthalate, methyl cellulose phthalate and mixtures thereof, cellulose acetate phthalate, hydroxypropyl methylcellulose succinate, ethyl cellulose succinate, methyl cellulose succinate and mixtures thereof, cellulose acetate trimellitate, cellulose ether phthalates; and polyvinyl acetate phthalate, succinate or trimellitate. A preferred enteric coating is Opadry OY-P 22920, available from Colorcon, 415 Moyer Blvd, West Point, Pa. 19486, United States of America. Enteric film-forming compositions are described, for example, in U.S. Pat. Nos. 4,556,552 and 4,704,295, the disclosures of which are incorporated herein by reference.

The method of the second embodiment provides a method for the treatment of constipation. The constipation may be associated, for example, with constipation-predominant IBS, pseudo obstruction or functional constipation.

In the method of the second embodiment, the mammal is typically a human.

In a method of the second embodiment, the colchicine and amino-salicylic acid derivative may be taken once, twice, three times a day or more frequently. The dosages may range for colchicine from 0.1 mg through to 5 mg per day, more typically 0.5 mg to 5 mg per day, still more typically 0.5 to 3 mg per day. The 5-ASA compound dosage may vary from 100 mg through to 5 g per day, more typically 200 mg to 4 g per day, still more typically 500 mg to 2 g per day.

Usually, the colchicine and the amino-salicylic acid derivative are administered twice daily. As a general rule for long term therapy the dosage may commence at a low level, such as daily and may be elevated to a higher dosage, such as twice or three times daily if required. Administration is typically over a period of from 30 days to 60 days or more, including indefinitely for the lifetime of the patient. More typically, a method of the invention results in relief of symptoms when the colchicine and the amino-salicylic acid derivative are administered over a period of from 60 days to 120 days. After relief or symptoms is achieved, administration of the colchicine and amino-salicylic acid derivative may be ceased, tapered, or reduced to lower maintenance dosages for an indefinite period.

Thus, a further form of the invention provides a pack including a plurality of compositions of the first embodiment in individual dosages having different amounts of the colchicine and the amino-salicylic acid derivative, the compositions being packaged in such a way that dosages of the colchicine and the amino-salicylic acid derivative are taken according to a predetermined schedule by a person to whom the dosages are administered.

For example, the compositions may be packaged in a blister pack in a strip, circle, or other arrangement facilitating sequential administration, with instruction that the compositions are to be taken by the patient in a particular order, commencing with a particular position in the pack. For example, if the compositions are packaged in a strip, typically administration commences with the first composition at one end of the strip and continues with successive compositions packaged along the strip, the amounts of colchicine and amino-salicylic acid derivative in the successive compositions varying according to a predetermined dosage regime. Other similar arrangements will suggest themselves readily to persons of ordinary skill in the relevant art.

Without wishing to be bound by any theory, it is postulated by the present inventor that both colchicine and amino-salicylic acid derivatives, such as 5-amino salicylic acid, are capable of secreting water into the bowel and are probably capable of suppressing abnormal bowel flora bacteria. Colchicine has anti-tubilin action and hence inhibits bacteria. 5-amino salicylic acid is a known antimicrobial agent similar to para-amino salicylic acid.

Best Method and Other Methods of Carrying Out the Invention

One preferred composition in accordance with the invention consists of 375 mg of olsalazine in a capsule also containing 0.8 mg of enterically coated colchicine. For example, the enterically coated colchicine may be obtained by microencapsulating a suitable quantity of granules of colchicine with Opadry OY-P 22920.

An alternative preferred composition in accordance with the invention is a capsule containing 375 mg of olsalazine and a 0.5 mg tablet of colchicine enterically coated with Opadry OY-P 22920.

In a preferred method in accordance with the invention for the treatment of severe constipation, a patient is administered with twice daily doses of 375 mg of olsalazine and 0.8 mg of enterically coated colchicine. Administration is continued twice daily until defecation is achieved. A patient with mild constipation may be administered once daily doses, in the morning, of 375 mg of olsalazine and 0.8 mg of enterically coated colchicine, whereas some patients with obstinate constipation may require three doses or more per day.

An enteric coating on the colchicine prevents the colchicine from being absorbed in the small bowel and reduces the danger of over-dosage. Hence the danger of the serious effects of overdose of colchicine which are known is avoided. In the colon, from which colchicine is not absorbed, it acts upon the bacteria relevant to constipation.

EXAMPLE

Composition Including 375 mg Olsalazine and 0.5 mg Colchicine

A. Enterically coated colchicine 0.5 mg tablets 1 kg of 100 mg tablets containing 0.5 mg colchicine (Colgout 0.5 mg tablets, Fisons Parmaceuticals) are sprayed in a suitable spray-coating apparatus with a 15% w/w solution of Opadry OY-P 22920 in aqueous ethanol (about 80% ethanol v/v) at an inlet air temperature of about 70–75° C. until the weight gain of the tablets is at least 8% of the weight of the uncoated core tablets.

B. Capsules of olsalazine and enterically coated cochicine

Capsules containing a coated tablet obtained from step A and a capsule of 375 mg olsalazine are prepared by conventional methods.

Case Studies

Case Study 1

A 48 year old patient who had been investigated for chronic abdominal pain, slow transit constipation with defecation occurring once a week, bloating, nausea and recurrent headaches was referred for treatment since she had failed to have symptoms controlled with anti-spasmodics and laxatives. Colonoscopy and stool cultures were all normal. In spite of the use of added fibre and laxatives together with antispasmodics and prokinetics she continued to suffer with her original symptoms. She was commenced on colchicine 0.5 mg twice daily together with olsalazine 250mg twice daily. Within 10 days of commencement of the treatment the patient began to defecate and by 3 weeks she was defecating normally with a marked reduction of abdominal pain, bloating and nausea. She was able to continue with the same relief on daily treatment for over 8 months.

Case Study 2

A 64 year old male who presented with bloating, abdominal pain—especially left iliac fossa, and defecation occurring every fourth to fifth day was referred alter previous investigations including stool tests, colonoscopy and transit studies had been carried out. He had slight transit constipation and had failed treatment with combined laxatives. This patient was commenced on colchicine 1 mg twice daily, together with olsalazine 250 mg twice daily. He began to defecate normally by 14 days and then to develop some loose motions. The colchicine was decreased to 0.5 mg in the morning and 1 mg at night and the olsalazine was continued at 250 mg twice daily. The patient's abdominal distension, abdominal pain and constipation were well-controlled. He continued the medication for 12 months, at which time reduction of the medication and ultimately ceasing the medication did not result in any recurrence of constipation. 3–6 months after ceasing medication the patient was not as loose as before, but he was able to defecate relatively normally every day or every second day.

This case provides an indication that the composition and method of the present invention can reverse the underlying problem; that is it can possibly eradicate or suppress the pathogenic bacteria that cause constipation.

Case Study 3

A 48 year old female suffering from chronic constipation, bloating and cramps was treated with olsalazine 250 mg twice per day and uncoated colchicine 0.5 mg 3 times per day. After about 10 days defecation commenced and the bloating and cramps were relieved. The regimen was changed to enterically coated colchicine 0.5 mg 3 times per day, with olsalazine continuing at 250 mg twice per day. The patient subsequently experienced loose motions and the colchicine was reduced to 0.5 mg enterically coated twice per day with maintenance of the olsalazine 250 mg twice per day. Following this change, the patient experienced normal motions and there was no loss of relief of the bloating and cramps.

What is claimed is:

1. A dosage form for use in the treatment or prophylaxis of constipation, comprising olsalazine present in an amount ranging from 100 mg to 1000 mg and colchicine present in an amount synergistically interacting with the olsalazine in the range of 0.1 mg to 3 mg.

2. A dosage form according to claim 1, comprising from 0.5 mg to 1.5 mg of colchicine and from 250 mg to 500 mg of olsalazine.

3. A dosage form according to claim 2, comprising from 0.5 to 1 mg of colchicine and from 250 mg to 500 mg olsalazine.

4. A method for the treatment or prophylaxis of constipation in a mammal in need of said treatment or prophylaxis, comprising administering to said mammal from 0.5 mg to 3 mg per day of colchicine and from 500 mg to 2 gm per day of olsalazine.

5. The method according to claim 4, comprising administering said mammal from 0.5 to 2 mg per day of colchicine and from 500 mg to 2 gm per day of olsalazine.

* * * * *